United States Patent
Roeder et al.

(10) Patent No.: US 10,765,406 B2
(45) Date of Patent: Sep. 8, 2020

(54) DEVICE AND METHOD FOR OBTAINING INFORMATION ABOUT ONE OR MORE LIVING BEINGS

(71) Applicant: Fraunhofer-Gesellschaft zur Foerderung der angewandten Forschung e.V., Munich (DE)

(72) Inventors: Olaf Roeder, Dresden (DE); Lars Schubert, Schoenteich ot Peterhain (DE); Constanze Tschoepe, Grossenhain (DE); Bernd Frankenstein, Ullersdorf (DE); Uwe Lieske, Dresden (DE)

(73) Assignee: Fraunhofer-Gesellschaft zur Foerderung der angewandten Forschung e.V., Munich (DE)

( * ) Notice: Subject to any disclaimer, the term of this patent is extended or adjusted under 35 U.S.C. 154(b) by 525 days.

(21) Appl. No.: 15/081,722

(22) Filed: Mar. 25, 2016

(65) Prior Publication Data
US 2016/0206286 A1 Jul. 21, 2016

Related U.S. Application Data

(63) Continuation of application No. PCT/EP2014/070575, filed on Sep. 25, 2014.

(30) Foreign Application Priority Data

Sep. 26, 2013 (DE) .................. 10 2013 219 474

(51) Int. Cl.
*A61B 8/08* (2006.01)
*A01M 1/02* (2006.01)
(Continued)

(52) U.S. Cl.
CPC .............. *A61B 8/48* (2013.01); *A01K 29/005* (2013.01); *A01M 1/026* (2013.01); *A01M 99/00* (2013.01);
(Continued)

(58) Field of Classification Search
CPC ........ A61B 8/48; A01K 29/005; A01M 1/026; A01M 99/00; G01N 29/4427
(Continued)

(56) References Cited

U.S. PATENT DOCUMENTS

| 4,671,114 A | 6/1987 | Litzkow et al. |
| 4,937,555 A * | 6/1990 | Litzkow ............... A01K 67/033 340/540 |

(Continued)

FOREIGN PATENT DOCUMENTS

| DE | 202011104613 U1 | 3/2012 |
| FR | 2825801 A1 | 12/2002 |

*Primary Examiner* — Kerri L McNally
(74) *Attorney, Agent, or Firm* — Michael A. Glenn; Perkins Coie LLP (57) ABSTRACT

Embodiments of the present invention provide a device for obtaining information about one or more living beings. The device comprises an actuator, a sensor and an evaluator. The actuator is configured to output an excitation signal for exciting the living being(s). The sensor is configured to detect a signal generated by the living being(s) in reaction to the excitation signal, to obtain a detected signal. The evaluator is configured to evaluate the detected signal so as to obtain the information about the living being(s).

9 Claims, 9 Drawing Sheets

(51) Int. Cl.
    *G01N 29/44*     (2006.01)
    *A01K 29/00*     (2006.01)
    *A01M 99/00*     (2006.01)

(52) U.S. Cl.
    CPC ............... *G01N 29/4427* (2013.01); *G01N 2291/02483* (2013.01)

(58) Field of Classification Search
    USPC ..................................................... 340/573.2
    See application file for complete search history.

(56) References Cited

U.S. PATENT DOCUMENTS

| | | | |
|---|---|---|---|
| 4,941,356 A * | 7/1990 | Pallaske | A01M 1/026 73/587 |
| 4,991,439 A | 2/1991 | Betts et al. | |
| 5,473,942 A | 12/1995 | Vick et al. | |
| 6,081,481 A * | 6/2000 | Sabatier | G01H 9/002 367/8 |
| 6,313,643 B1 * | 11/2001 | Tirkel | G01N 22/00 119/721 |
| 6,801,131 B2 * | 10/2004 | Donskoy | G01N 33/46 324/637 |
| 7,271,706 B2 | 9/2007 | Lee et al. | |
| 2004/0193376 A1 | 9/2004 | Rodriguez Gobernado et al. | |
| 2008/0255806 A1 * | 10/2008 | Sambuelli | G01M 5/0025 702/183 |
| 2009/0303053 A1 | 12/2009 | Evans et al. | |

* cited by examiner

DEVICE AND METHOD FOR OBTAINING INFORMATION ABOUT ONE OR MORE LIVING BEINGS

CROSS-REFERENCE TO RELATED APPLICATIONS

This application is a continuation of copending International Application No. PCT/EP2014/070575, filed Sep. 25, 2014, which claims priority from German Application No. 10 2013 219 474.9, filed Sep. 26, 2013, which are each incorporated herein in its entirety by this reference thereto.

BACKGROUND OF THE INVENTION

Embodiments of the present invention relate to a device and a method for obtaining information about one or more living beings. Further embodiments relate to a method and a device for selectively exciting, detecting and monitoring animal populations such as insects, for example, as well as for determining specific states of development and behavior.

One area where detection and/or monitoring of animal populations are useful is pest monitoring and pest control.

More than 10% of global grain harvest is destroyed by animal pests. Said losses amount to about 200 million tons of foodstuff and animal food per year worldwide. The resulting economic damage amounts to about 20 billion euros per year worldwide. In Germany alone, about 40 million tons of grain are stored each year. The food regulation stipulates that mills and food processing companies do not accept and/or process any products containing animal pests. For example, the most dangerous storage pest in Europe is the granary weevil.

There are various methods of recognizing animal pests in bulk material such as grain, for example. In a known method, sensitive stem microphones are inserted into the bulk material, and in the event of pest infestation, corresponding acoustic signals such as nibbling sounds, for example, are received. The nibbling sounds caused by the insects, in particular by the insect larvae, may be recognized and evaluated in a manual or (semi-) automated manner.

However, by means of the known methods of recognizing animal pests, the pests in their various stages of development can only be detected when they cause or emit noises at the time of measurement. However, the pest's activities are highly dependent on the ambient temperature. For example, recognition of the pests is not or hardly possible in the event of a reduced temperature.

In addition, it has to be taken into account that different pests cause different noises. By means of the known methods of recognizing animal pests, said noises virtually cannot be differentiated, i.e., the type of pests cannot be determined by means of the known methods.

In addition, it has to be taken into account that pests typically live through several stages of development (e.g., the granary weevil lives through four stages of development) and accordingly emit noises that differ in amplitude and frequency as a function of the stage of development. By means of the known methods of recognizing animal pests, said noises virtually cannot be differentiated into different stages of development.

Moreover, by using current methods it is not possible to recognize an extent of an infestation with pests and to determine a location of a beginning infestation with pests, e.g., in a silo.

In summary, it is therefore not possible, by means of the known methods of recognizing animal pests, to early initiate and perform, in a targeted manner, pest control that is adapted in a manner defined by the type of pest, the stage of development, the extent of infestation and the location of settlement, and that is adequate in terms of effort and cost, by permanently monitoring stocks.

A further area where detection and/or monitoring of animal populations are useful is monitoring of working animals, such as monitoring of bees in bee-keeping.

The direct benefit supplied by honey bees kept by bee-keepers consists in the production of honey, wax, propolis and pollen. Worldwide production of honey amounts to about 1.5 million tons per year. About 80 million bee colonies are kept by bee-keepers worldwide. The indirect benefit of honey bees consists in the transfer of the pollen by the activity of collecting nectar and pollen and is many times higher than their direct services that they render by producing honey. The economic benefit of pollination per year is estimated to exceed 100 billion U.S. dollars worldwide. The internationally largest honey producers who have the largest numbers of bee colonies are (in the order given) China, U.S., Argentina, Mexico, Canada and Brazil. In Germany, about one quarter of the annual German consumption of honey is produced by about 100,000 bee-keepers possessing about one million bee colonies. The remainder is imported. Large honey farms in Europe often keep 300 or more bee colonies, in the US they often keep 1,000 or more bee colonies.

For bee-keepers, monitoring the bee colonies and keeping them in a manner that takes animal welfare into account constitutes an enormous amount of effort which becomes more difficult or even impossible to manage as the number of bee colonies increases. Bee-keeping is made substantially more difficult by parasites such as the *Varroa* mite, by highly infectious diseases such as the American foul brood and by the heavy use of pesticides in agriculture. Therefore, bee-keepers obtain information about any of their colonies, ideally at any time, with regard to specific states such as the mental state, the swarming behavior, losses of bees, diseases, behavioral disorders, etc.

No methods of monitoring working animals are known which enable effective (semi-) automated monitoring of bee colonies. Therefore, bee-keepers who migrate with their bee colonies, i.e., who take their bee colonies to and install them wherever plants are blossoming and a good yield can be found, have to be on site in order to monitor and manage the bee colonies, which represents a significant amount of effort.

SUMMARY

According to an embodiment, a device for acquiring information about one or more living beings may have: an actuator for outputting an excitation signal for exciting the living being(s); a sensor for detecting a signal generated by the living being(s) in reaction to the excitation signal, so as to acquire a detected signal; and an evaluator for evaluating the detected signal so as to acquire the information about the living being(s).

According to another embodiment, a device for acquiring information about a pest or several pests within a bulk material may have: an actuator for outputting an excitation signal for exciting the bulk material, the pest or the pests; a sensor for detecting a signal generated in response to the excitation, so as to acquire a detected signal; an evaluator for evaluating the detected signal so as to acquire the information about the pest(s) within the bulk material.

According to another embodiment, a system may have: an inventive device; and an accommodator for accommodating a commodity, the device being arranged at or within the accommodator such that a commodity accommodated by the accommodator can be monitored by means of the device; or accommodator for accommodating one or more living beings, the device being arranged at or within the accommodator such that one or more living beings can be monitored by means of the device.

According to another embodiment, a method of acquiring information about one or more living beings may have the steps of: outputting an excitation signal for exciting the living being(s); detecting a signal generated by the living being(s) in reaction to the excitation signal, so as to acquire a detected signal; and evaluating the detected signal so as to acquire the information about the living being(s).

According to another embodiment, a method of acquiring information about a pest or several pests within a bulk material may have the steps of: outputting an excitation signal for exciting the bulk material or the pest(s); detecting a signal generated in response to the excitation, so as to acquire a detected signal; and evaluating the detected signal so as to acquire the information about the pest(s) within the bulk material.

According to another embodiment, a non-transitory digital storage medium may have a computer program stored thereon to perform the inventive methods when said computer program is run by a computer.

Embodiments of the present invention provide a device for obtaining information about one or more living beings. The device comprises an actuator, a sensor and an evaluator. The actuator is configured to output an excitation signal for exciting the living being(s). The sensor is configured to detect a signal generated by the living being(s) in reaction to the excitation signal, to obtain a detected signal. The evaluator is configured to evaluate the detected signal so as to obtain the information about the living being(s).

The present invention is based on the idea of emitting, by means of an actuator, an excitation signal for exciting the living being(s) (e.g., insects) and to detect and evaluate a signal generated by the living being(s) in reaction to the excitation signal, rather than a random signal that is dependent on external parameters (such as the temperature and air humidity), so as to obtain the information about the living being(s).

Further embodiments provide a system comprising the above-described device for obtaining information about one or more living beings and a means for accommodating a commodity. The device is arranged at or within the means such that the commodity accommodated by the means can be monitored by means of the device.

Further embodiments provide a system comprising the above-described device for obtaining information about one or more living beings and a means for accommodating one or more living beings. The device is arranged at or within the means such that one or more living beings accommodated by the means can be monitored by means of the device.

Further embodiments provide a method of obtaining information about one or more living beings. The method includes outputting an excitation signal for exciting the living being(s). Moreover, the method includes detecting a signal generated by the living being(s) in reaction to the excitation signal, so as to obtain a detected signal. In addition, the method includes evaluating the detected signal so as to obtain the information about the living being(s).

Further embodiments provide a device for obtaining information about a pest or several pests in bulk material. The device includes an actuator for outputting an excitation signal for exciting the bulk material, the pest or pests, a sensor for detecting a signal generated in response to the excitation, so as to obtain a detected signal, and an evaluator for evaluating the detected signal so as to obtain the information about the pest(s) within the bulk material.

BRIEF DESCRIPTION OF THE DRAWINGS

Embodiments of the present invention will be detailed subsequently referring to the appended drawings, in which:

FIG. 6b shows a spectrogram of the detected signal shown in FIG. 6a;

DETAILED DESCRIPTION OF THE INVENTION

In the below description of the embodiments of the invention, elements which are identical or have identical actions will be provided with the same reference numerals in the figures, so that their descriptions will be interchangeable in the different embodiments.

Figure 1:
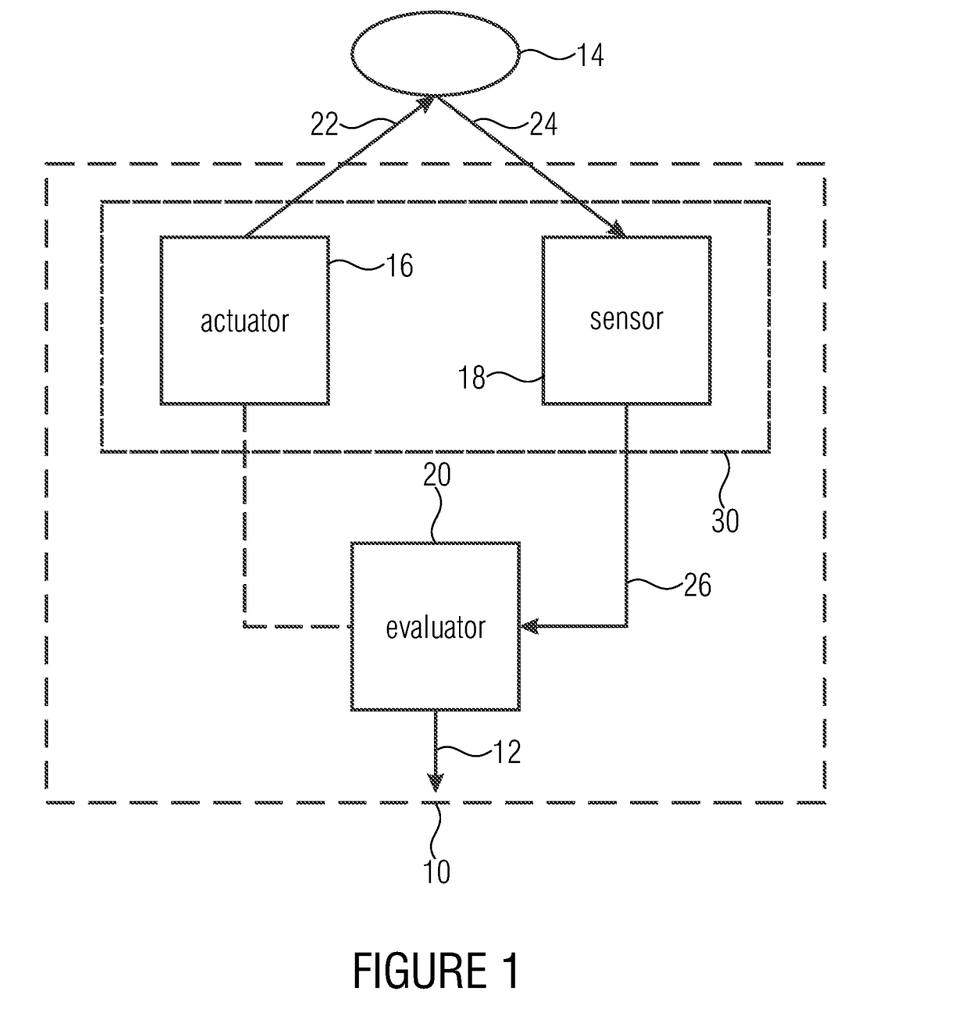
FIG. 1 shows a schematic block diagram of a device for obtaining information about one or more living beings, in accordance with an embodiment of the present invention.

FIG. 1 shows a schematic block diagram of a device 10 for obtaining information 12 about one or more living beings 14. The device 10 comprises an actuator 16, a sensor 18 and an evaluator 20. The actuator 16 is configured to output an excitation signal 22 for exciting the one or more living beings 14. The sensor 18 is configured to detect a signal 24 generated by the one or more living beings 14 in reaction to the excitation signal 22, so as to obtain a detected signal 26. The evaluator 20 is configured to evaluate the detected signal 26 so as to obtain the information 12 about the one or more living beings 14.

The present invention is based on the idea of outputting, by means of an actuator 16, an excitation signal 22 for exciting the one or more living beings 14, and to detect and evaluate a signal 24 generated by the one or more living beings 14 in reaction to the excitation signal 22, rather than a random signal that is dependent on external parameters (such as the temperature and air humidity), so as to obtain the information 12 about the living beings 14.

In embodiments, the device 10 may be configured, for example, to monitor a commodity, it being possible for the information 12 about the one or more living beings 14 to indicate whether or not the commodity monitored by means of the device 10 is infested with the one or more living beings 14.

The commodity monitored by means of the device 10 may be a foodstuff (e.g., grain), animal food, a building, a construction, natural wood, a wooden structure (e.g., a stack of wood, sawn wood or a wooden building), a field or a piece of forest, while the living being 14 may be a pest, for example.

In embodiments, the device 10 may be configured, for example, to monitor the one or more living beings 14, the information 12 about the one or more living beings 14 indicating a state of the one or more living beings 14.

For example, the living beings 14 to be monitored may be working animals, e.g., bees, while the state concerning the living beings 14 may be a behavioral disorder, a loss or a disease, for example.

In embodiments, the actuator 16 may be configured to output an acoustic excitation signal as the excitation signal 22. The excitation signal 22 may comprise one or more frequencies. The frequency or frequencies may be fixed or variable (e.g., rising, falling or chirped). The frequency or frequencies may be within the infrasonic frequency range (below about 16 Hz), within the audible frequency range (from about 16 Hz to 20 kHz) or within the ultrasonic frequency range (above about 16 kHz). Moreover, the excitation signal 22 may comprise a frequency range that is within the infrasonic frequency range, within the audible frequency range or within the ultrasonic frequency range. In addition, the excitation signal 22 may be band-limited, an upper limiting frequency of the excitation signal 22 not exceeding 16 Hz, 16 kHz, 20 kHz, 100 kHz, 500 kHz or 1 GHz.

The signal 24 generated by the one or more living beings 14 in reaction to the excitation signal 22 may also be an acoustic signal which may also comprise a frequency or several frequencies that may be within the infrasonic frequency range, the audible frequency range and/or the ultrasonic frequency range.

Accordingly, the sensor 18 may be configured to detect a signal 24 that is within the infrasonic frequency range, the audible frequency range and/or the ultrasonic frequency range.

In embodiments, the actuator 16 and the sensor 18 may be implemented in a shared means, device or unit 30, as is outlined in FIG. 1. In other words, the device 10 may comprise an actuator/sensor combination 30 which includes the actuator 16 and the sensor 18.

For example, the actuator/sensor combination 30 shown in FIG. 1 may be configured for acoustically exciting 22 the one or more living beings 14 (e.g., an animal population) within the low-frequency and/or high-frequency (ultrasound) wavelength range 22 and for receiving acoustic signals 24 emitted by the one or more living beings (e.g., the animal population) 14.

In embodiments, the evaluator 20 may be configured to classify the detected signal 26 so as to obtain the information 12 about the one or more living beings 14. To this end, the evaluator 20 may comprise a memory, for example, where reference signals (e.g., typical sound patterns) are stored or can be stored, it being possible for the evaluator 20 to be configured to classify the detected signal 26 while using the reference signals. For example, at least one reference signal may be stored for each class within the memory, it being possible for the evaluator 20 to be configured to compare the detected signal 26 to the reference signals so as to classify the detected signal.

In addition, the evaluator 20 may include a system for classifying sound events, it being possible for the actuator/sensor combination 30 to be connected to the system for classifying the sound events. Moreover, the evaluator 20 may comprise a database containing typical sound patterns, it being possible for the actuator/sensor combination 30 and the system for classifying the sound events to be connected to the database.

Figure 2:
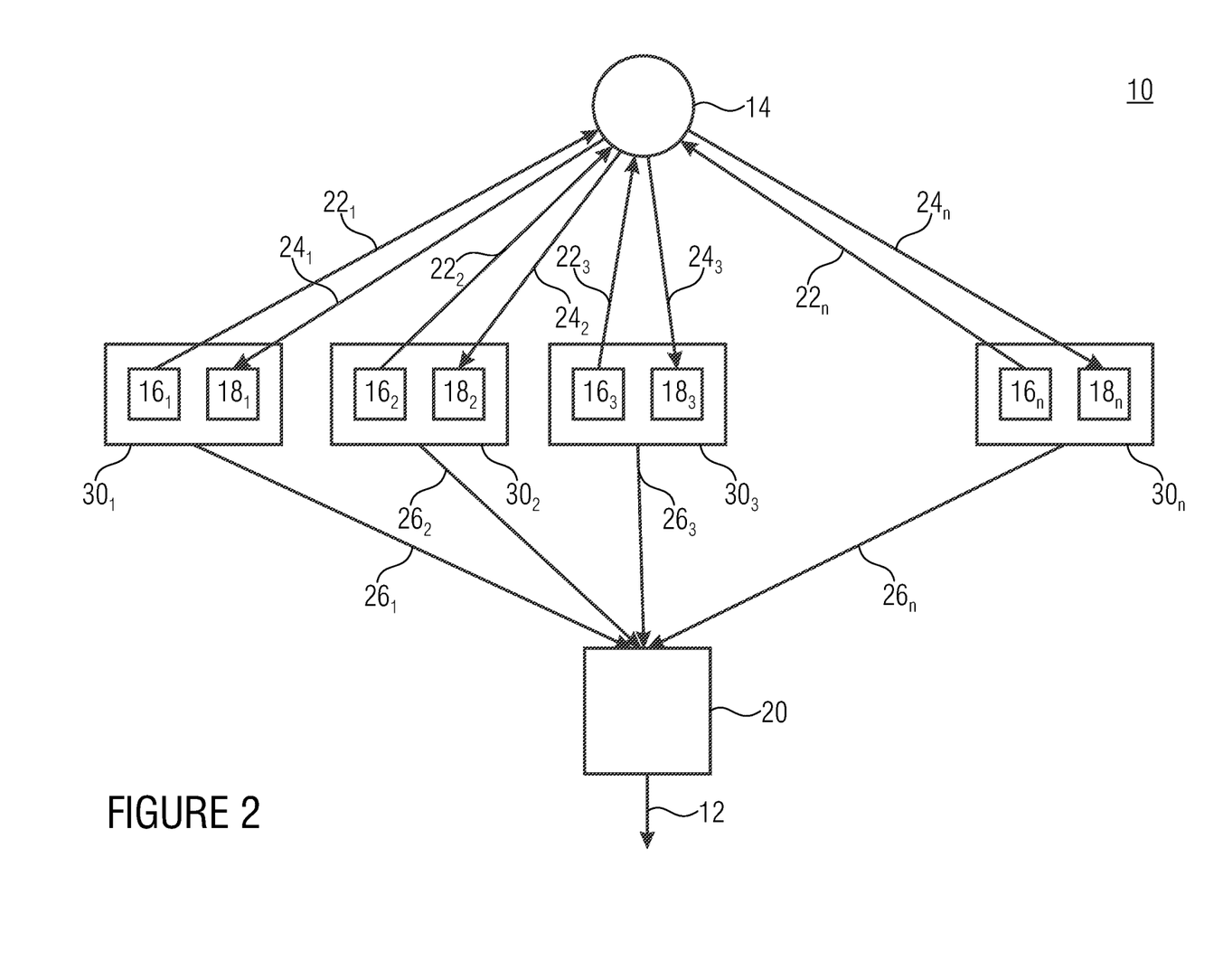
FIG. 2 shows a schematic block diagram of a device for obtaining information about one or more living beings, in accordance with an embodiment of the present invention.

FIG. 2 shows a schematic block diagram of a device 10 for obtaining information 12 about one or more living beings 14. As can be seen in FIG. 2, the device may comprise n actuators $16_1$ to $16_n$ and n sensors $18_1$ to $18_n$, n being a natural number larger than or equal to one, $n \geq 1$. The actuators $16_1$ to $16_n$ may be configured to output excitation signals $22_1$ to $22_n$ for exciting the one or more living beings 14. The sensors $18_1$ to $18_n$ may be configured to detect a signal $24_1$ to $24_n$ generated by the living being(s) 14 in reaction to at least one of the excitation signals $22_1$ to $22_n$, so as to obtain detected signals $26_1$ to $26_n$. The evaluator 20 may be configured to evaluate the detected signals $26_1$ to $26_n$ so as to obtain the information 12 about the living being(s) 14.

As can be seen in FIG. 2, the actuators $16_1$ to $16_n$ and/or sensors $18_1$ to $18_n$ may be arranged in an array. In this context, the device 10 may be configured to generate a pivotable excitation signal lobe by the excitation signals $22_1$ to $22_n$ output by the actuators $16_1$ to $16_n$.

Moreover, one actuator of the actuators $16_1$ to $16_n$ and one sensor of the sensors $18_1$ and $18_n$ in each case may be implemented in a shared means, device or unit $30_1$ to $30_n$. In other words, the device 10 may comprise n actuator/sensor combinations $30_1$ to $30_n$, each actuator/sensor combination of the actuator/sensor combinations $30_1$ to $30_n$ including, or having, one actuator of the actuators $16_1$ to $16_n$ and one sensor of the sensors $18_1$ to $18_n$.

In embodiments, at least one actuator/sensor combination 30 (see FIG. 1) or an array of actuator/sensor combinations $30_1$ to $30_n$ (see FIG. 2) may be arranged in accordance with the spatial conditions and/or the sound propagation rate at hand.

Moreover, at least one actuator/sensor combination 30 (see FIG. 1) or an array of actuator/sensor combinations $30_1$ to $30_n$ (see FIG. 2) may be arranged on an internal and/or external wall of a housing (e.g., of a container, a silo, a ship's cargo hold or an animal's dwelling).

In addition, at least one actuator/sensor combination 30 (see FIG. 1) or an array of actuator/sensor combinations $30_1$ to $30_n$ (see FIG. 2) may be arranged within an interior of a housing (e.g., of a container, a silo, a ship's cargo hold or an animal's dwelling) at sound-amplifying media such as metal sheets, partition walls or sound funnels.

In embodiments, the device 10 may be configured to pivot, by means of a multiple arrangement of actuator/sensor combinations $30_1$ to $30_n$, sound lobes during transmission and to exploit amplification effects that are due to wave interference (phased-array technology).

Moreover, the device 10 may be configured to determine, by means of a multiple arrangement of actuator/sensor combinations $30_1$ to $30_n$, sound velocities in the stored commodity (e.g., material or raw material) or in the animal population to be monitored, and to calibrate the device 10 accordingly.

Figure 3:
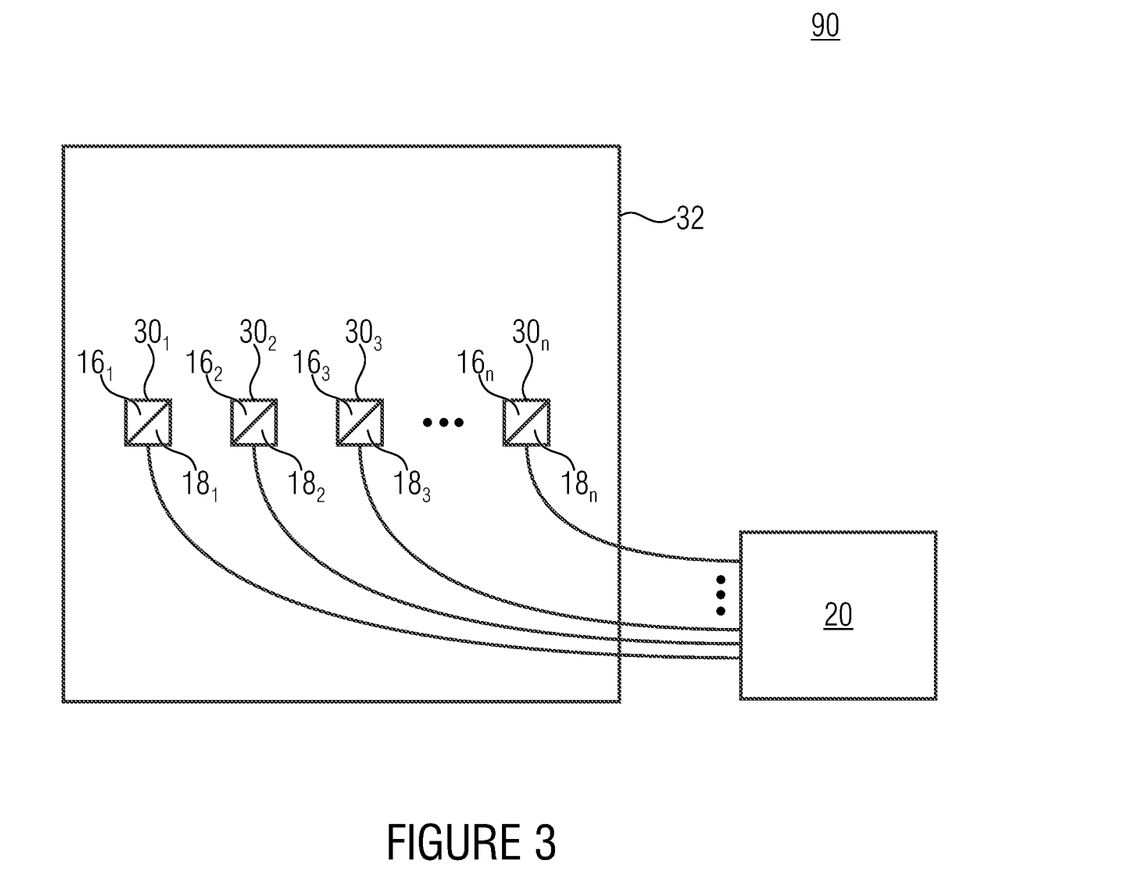
FIG. 3 shows a schematic view of a system 90 in accordance with an embodiment of the present invention.

FIG. 3 shows a schematic view of a system 90 in accordance with an embodiment of the present invention.

The system 90 comprises the above described device 10 and means 92 for accommodating a commodity, or means 92 for accommodating one or more living beings.

The device 10 includes at least one actuator $16_1$ to $16_n$ and at least one sensor $18_1$ to $18_n$. Of course, the device may also include at least one actuator/sensor combination $30_1$ to $30_n$.

As is shown in FIG. 3, the at least one actuator $16_1$ to $16_n$ and the at least one sensor $18_1$ to $18_n$ (or the at least one actuator/sensor combination $30_1$ to $30_n$) may be arranged (e.g., connected) at or within the means 90 such that the commodity accommodated by the means 90, and/or the living being(s) 14 accommodated by the means 90 can be monitored by means of the device.

Moreover, the actuators 16 and/or sensors 18 (or actuator/sensor combinations 30) may be arranged inside media such as spheres, cylinders or the like (self-sufficient systems) which are initially not connected to the surroundings and—for the purpose of performing the inventive method—abut on walls or are carried along with the product within the stream of bulk material.

The actuators 16 and/or sensors 18 (or actuator/sensor combinations 30) may be connected to an external evaluator 10 in this context.

For example, the actuators 16 and/or sensors 18 (or actuator/sensor combinations 30) may be connected to the receiving and evaluating unit 20 by electric conductors (cable connection), by optical conductors (optical coupling) or by electromagnetic radiation (radio communication). Energy may also be supplied via said connection. Of course, the actuators 16 and/or sensors 18 (or actuator/sensor combinations 30) may also be supplied with energy by means of a battery, an accumulator and/or a method of energy harvesting.

Moreover, the actuators 16 and/or sensors 18 (or actuator/sensor combinations 30) may be combined with a system for moisture measurement, temperature measurement and/or optical measurement for quality assessment purposes.

The means 90 may be a container, a silo, a ship's cargo hold or an animal's dwelling.

Figure 4:
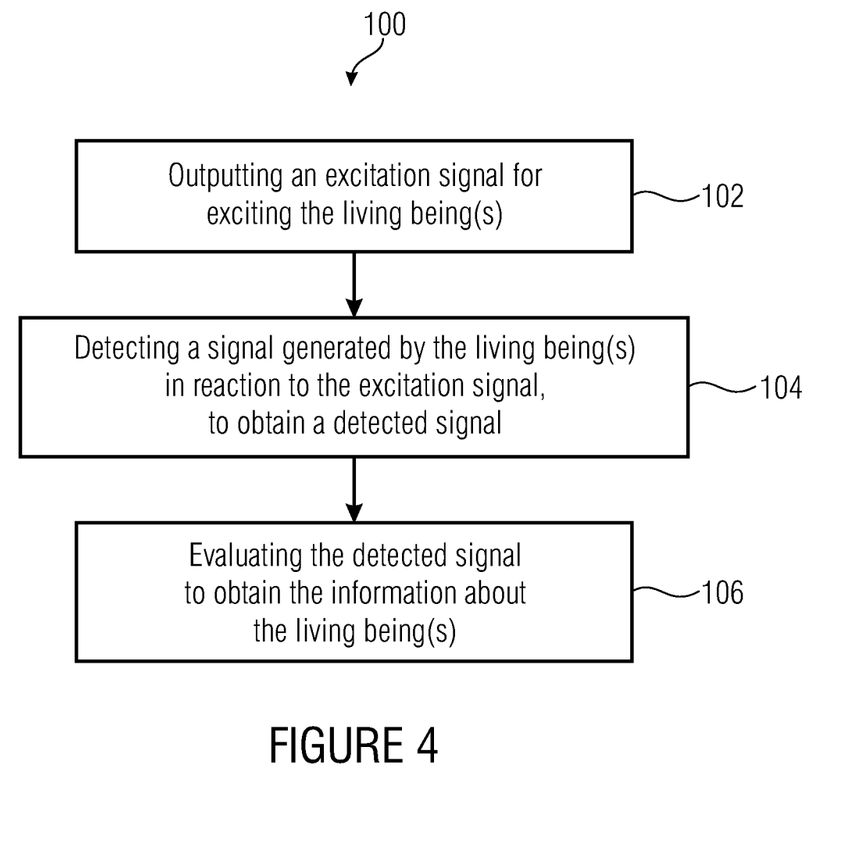
FIG. 4 shows a flow chart of a method of obtaining information about one or more living beings, in accordance with an embodiment of the present invention.

FIG. 4 shows a flow chart of a method 100 of obtaining information 12 about one or more living beings 14. The method 100 includes outputting 102 an excitation signal 22 for exciting the living being(s) 14. Moreover, the method 100 includes detecting 104 a signal 24 generated by the living being(s) 14 in reaction to the excitation signal 22, so as to obtain a detected signal 26. Moreover, the method 100 includes evaluating 106 the detected signal 26 so as to obtain the information 12 about the living being(s) 14.

In embodiments, the method 100 includes a combination of acoustic excitation of the living being(s), e.g., an animal population, within the low-frequency and/or high-frequency (ultrasound) wavelength range (e.g., by the actuator 16 shown in FIG. 1) and reception of acoustic signals 24 emitted by the living being(s) 14 (e.g., animal population) within the range of low-frequency and/or high-frequency waves (e.g., by the sensor 18 shown in FIG. 1) in combination with methods of localizing and classifying said sound events.

Excitation of the animal(s) (e.g., animal population) 14 may be effected within the fixed or tuned frequency range, depending on the ambient conditions and the sound propagation at hand and on the type of living being(s) (e.g., animal species or pest species).

The method 100 is based on transmitting/receiving by means of at least one combined actuator/sensor 30 (see FIG. 1), advantageously by means of an array (multiple arrangement) of combined actuators/sensors $30_1$ to $30_n$ (see FIG. 2) arranged in compliance with the spatial conditions.

The method of implementing a multiple arrangement of actuators/sensors $30_1$ to $30_n$ enables pivoting of sound lobes during transmission and exploiting amplification effects that are due to wave interference (phased-array technology).

In addition, the method of implementing a multiple arrangement of actuators/sensors $30_1$ to $30_n$ enables determining sound velocities within the stored commodity (e.g., material or raw material) and/or within the animal population, and adjusting the method accordingly.

The type of arrangement and implementation of the actuator/sensor combination $30_1$ to $30_n$ enables exciting the living being(s) (e.g., animal population) 14 at low frequencies, for example, and receiving high frequencies, or vice versa, as well as operating within similar and/or identical frequency ranges.

The above described method 100 (which may comprise a classification of the received sound waves, for example) enables monitoring and controlling of pests 14. For example, the existence of a pest infestation 14 may be determined, or ascertained. Moreover, a type of the pests 14 may be determined. In addition, an extent or degree of the pest infestation may be determined. Furthermore, a location of settlement and/or a position within the room infested with the pests 14 may be determined. The method 100 may further include filtering of the relevant noises from ambient and/or interference noises.

In addition, the above described method 100 (which may comprise, e.g., a classification of the received sound waves) enables monitoring of working animals, e.g., in bee-keeping. For example, different states such as nervousness, hunger, the presence of queen bees about to hatch, swarming behavior, parasite infestation, alien animals (e.g., rodents), for example, can be recognized. The method 100 may further include filtering of the relevant noises from ambient and/or interference noises.

Moreover, the above described method 100 enables pest monitoring for natural wood and wooden structures (stacks of wood, sawn wood, wooden buildings) prior to, during as well as following processing, and enables quarantine monitoring and pest monitoring in forests (living trees, dead wood), e.g., by installing sleeves supporting actuator/sensor combinations 30).

Figure 5:
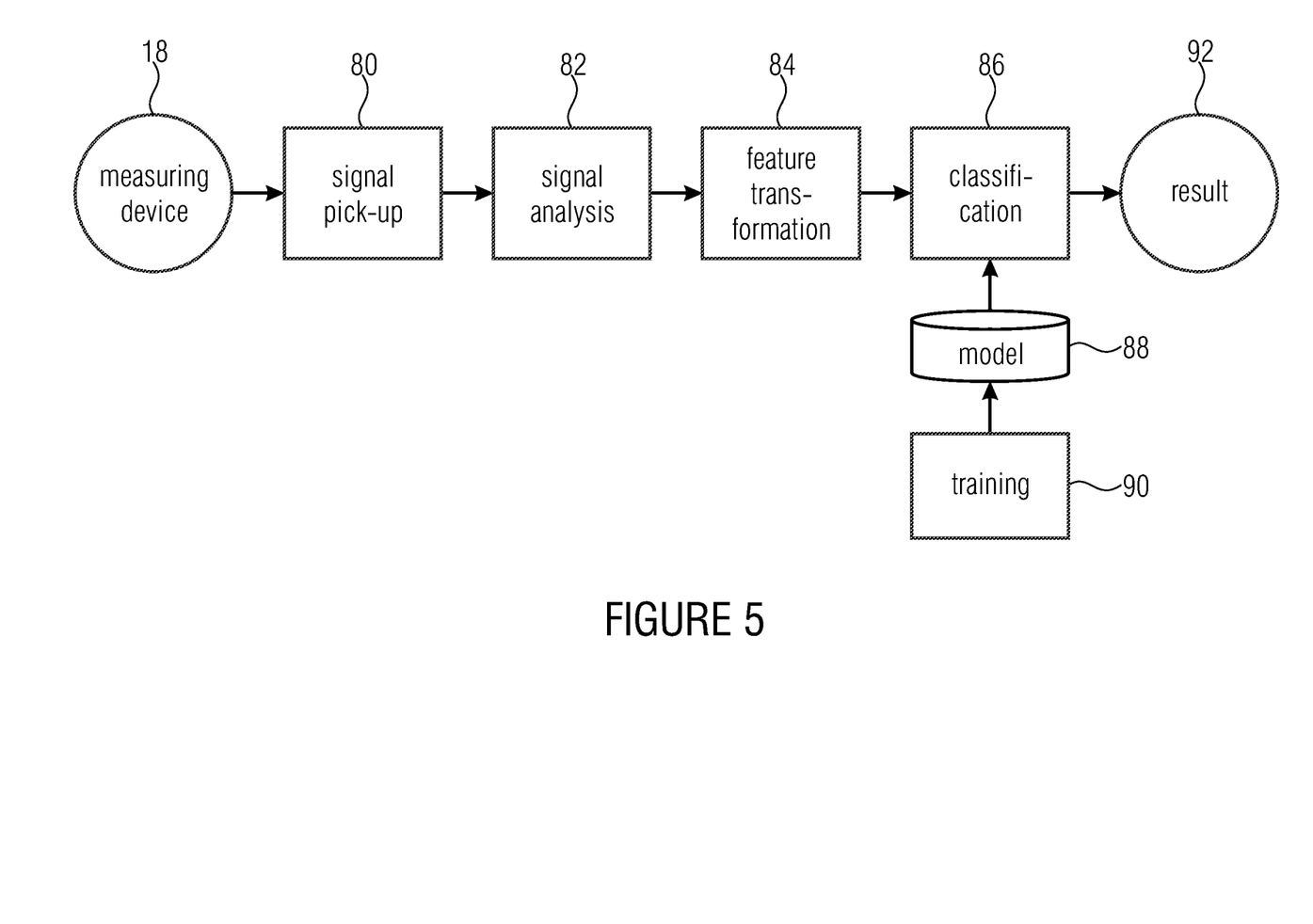
FIG. 5 shows a flow chart of a method of acoustic pattern recognition.

FIG. 5 shows a flow chart of a method of acoustic pattern recognition. In a first step 80, signal pick-up may occur by means of a measuring device 18. In a second step 82, signal analysis may take place. In a third step 84, feature transformation may occur. In a fourth step 86, a classification may be performed, e.g., on the basis of a model 88 which may have been acquired by a training 90, so as to obtain a result 92.

Thus, an embodiment of acoustic pattern recognition involves statistical sequence classification with hidden Markov models. However, other methods of acoustic pattern recognition may also be employed.

In addition, the acoustic method may be combined with a method of humidity measurement and/or temperature measurement and/or an optical measuring method for quality assessment purposes.

Further embodiments provide a device 10 for obtaining information 12 about a pest or several pests 14 in bulk material. The device 10 includes an actuator 16 for outputting an excitation signal 22 for exciting the bulk material, the pest or pests 14, a sensor 18 for detecting a signal 24 generated in response to the excitation, so as to obtain a detected signal 26, and an evaluator 20 for evaluating the detected signal 26 so as to obtain the information 12 about the pest(s) 14 within the bulk material.

In this context, the generated signal 24 may be generated by the pest(s) in reaction to the excitation signal 22.

Moreover, the generated signal 24 may be dependent on a resonant frequency (or several resonant frequencies) of the bulk material, the resonant frequency of the bulk material being dependent on an infestation of the bulk material with the pest(s).

The resonant frequency of the bulk material is dependent on the resonant frequency, or natural frequency, of the individual elements (e.g., grains) of the bulk material. For example, grains of the bulk material that are infested may have a different resonant frequency, or natural frequency, than non-infested grains. The resonant frequency of the bulk material may thus be shifted in the event of infestation with the pest(s). Moreover, it is also possible for the bulk material to comprise more than one resonant frequency due to the fact that some grains may be infested and some may not.

Thus, it is possible to either excite the pest(s) by means of the excitation signal 22 and to detect a signal 24 generated by the pest(s) in reaction to the excitation signal, or to excite the bulk material and to detect, in response to the excitation of the bulk material, a signal which is dependent on the resonant frequency (or natural frequency) of the bulk material. Of course, it is possible to excite both the pest(s) and the bulk material at the same time, in which case the generated signal is (partly) generated by the pest(s) and additionally is dependent on the resonant frequency (or natural frequency) of the bulk material.

Moreover, the actuator 16 may be configured to tune a frequency of the excitation signal 22 to a resonant frequency of the bulk material.

Furthermore, the sensor 18 may be configured to detect a reference signal independent of the excitation so as to obtain a detected reference signal; the evaluator 20 may further be configured to evaluate the detected reference signal so as to obtain the information 12 about the pest(s) 14 present within the bulk material.

For example, the sensor 18 may be configured to detect the reference signal (temporally) prior to or following excitation of the bulk material and/or of the pest(s). The evaluator 20 may be configured, for example, to compare the detected reference signal to the detected signal 26 so as to obtain the information 12 about the pest(s) 14 present within the bulk material.

Some pests increase their activities in response to the excitation signal, so that the generated signal 24 comprises additional signal components as compared to the reference signal, whereas other pests reduce or even stop their activities in response to the excitation signal, so that certain signal components are reduced or are even missing within the generated signal 24 as compared to the reference signal.

Figure 6A:
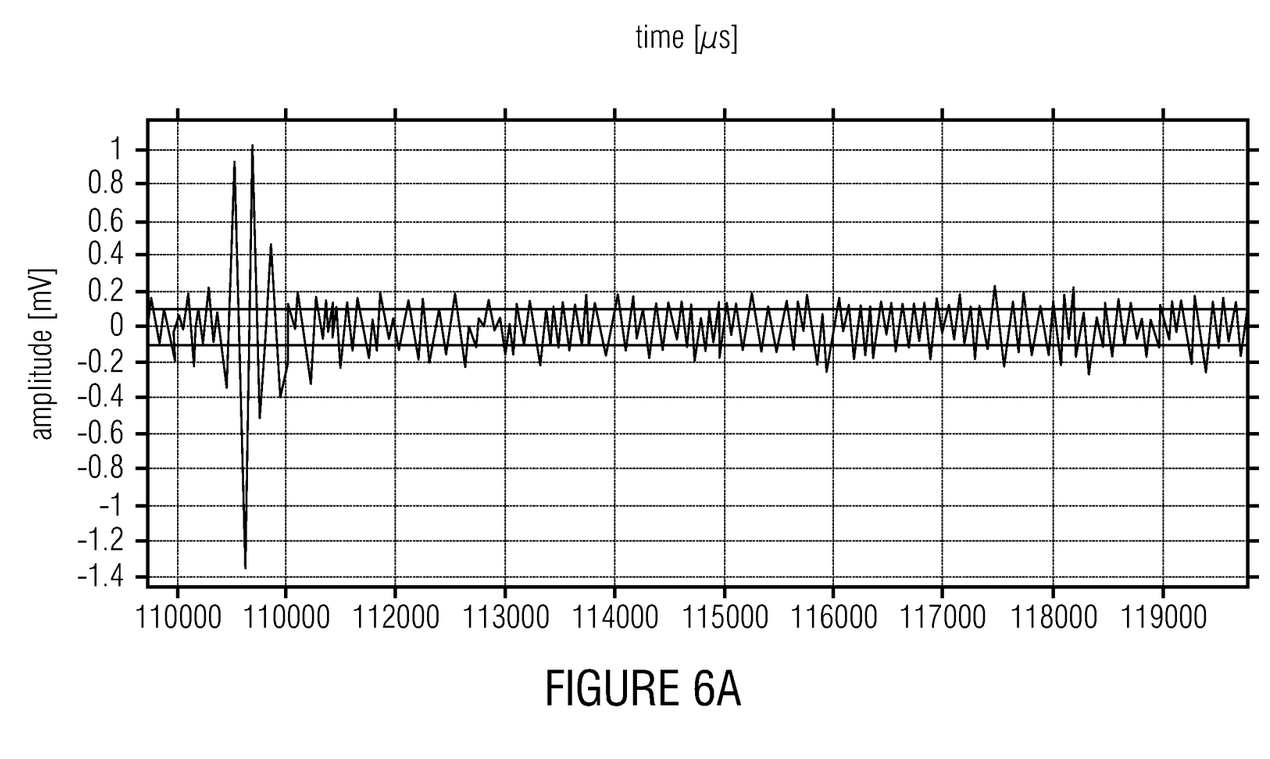
FIG. 6a shows, in a diagram, an amplitude of the detected signal plotted over time by using the example of a larva of the species of *Sitophilus granarius* (granary weevil)

FIG. 6a shows, in a diagram, an amplitude of the detected signal in mV plotted over time in s by using the example of a larva of the species *Sitophilus granarius* (granary weevil).

Figure 6B:
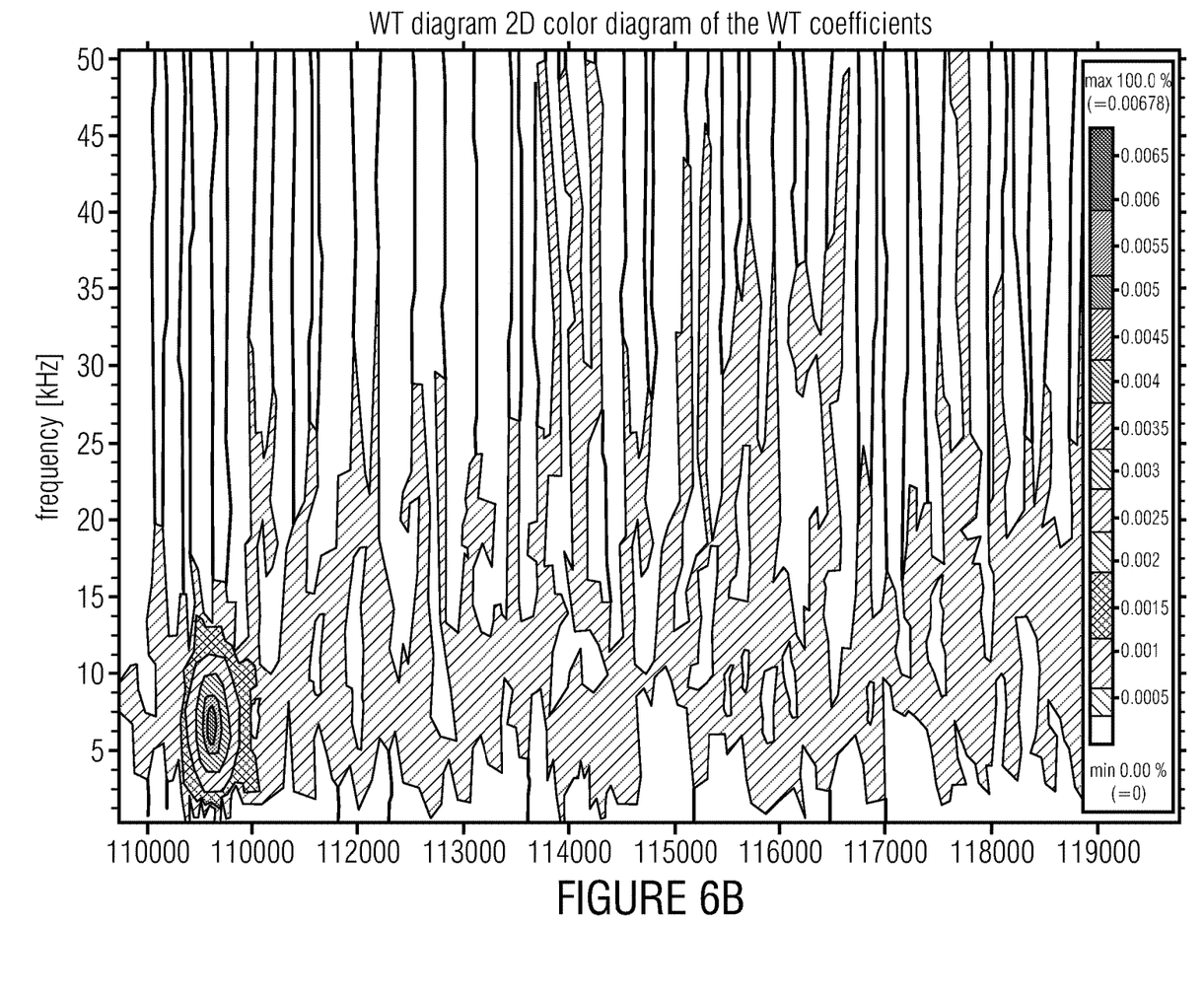

FIG. 6b shows a spectrogram of the detected signal shown in FIG. 6a. In FIG. 6b, the ordinate describes the frequency in kHz, while the abscissa describes time in s, and the color and/or hatching gradient describes X in %.

Figure 6C:
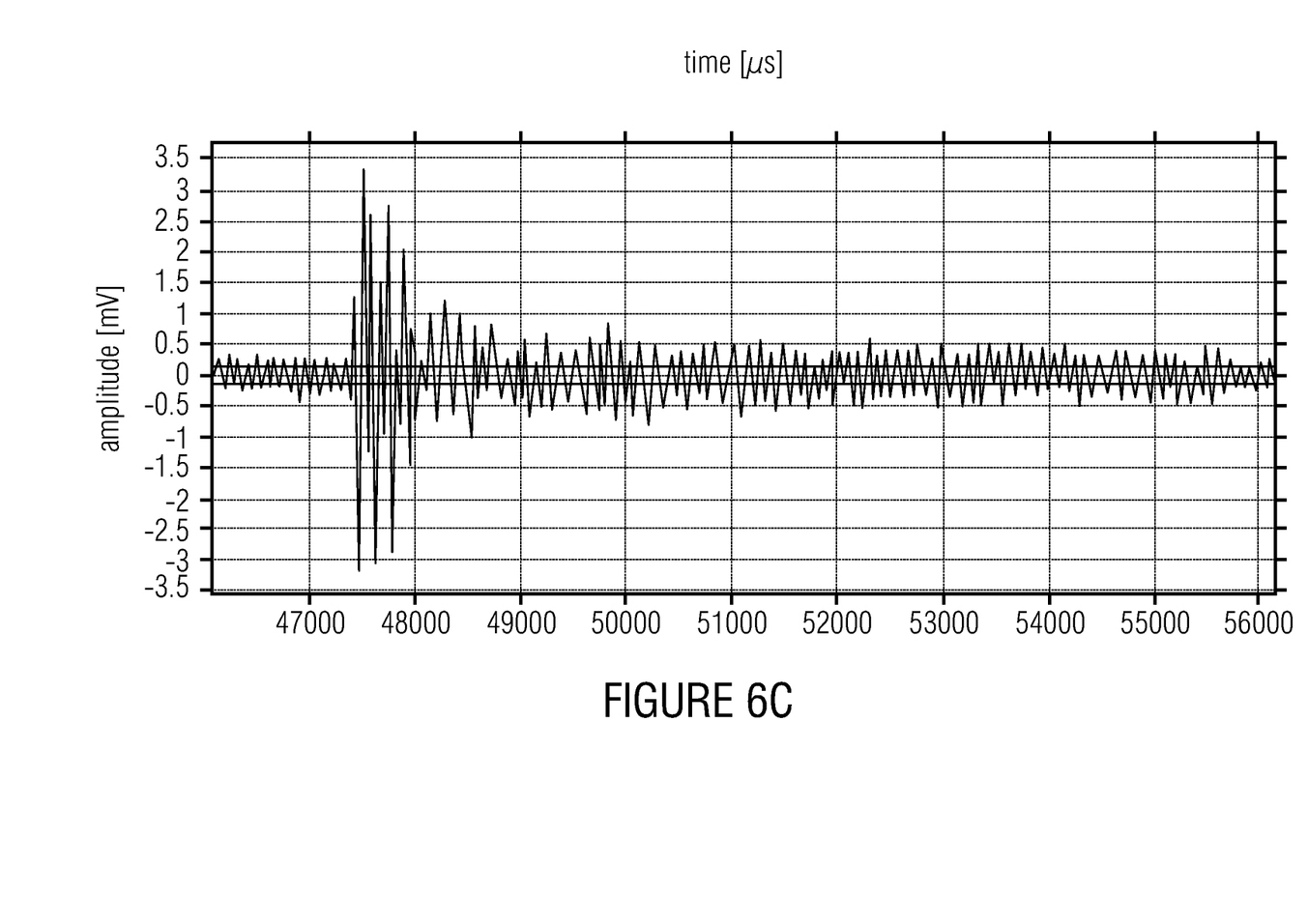
FIG. 6c shows, in a diagram, an amplitude of the detected signal plotted over time by using the example of a beetle of the species of *Sitophilus granarius* (granary weevil)

FIG. 6c shows, in a diagram, an amplitude of the detected signal in mV plotted over time in s by using the example of a beetle of the species of *Sitophilus granarius* (granary weevil).

Figure 6D:
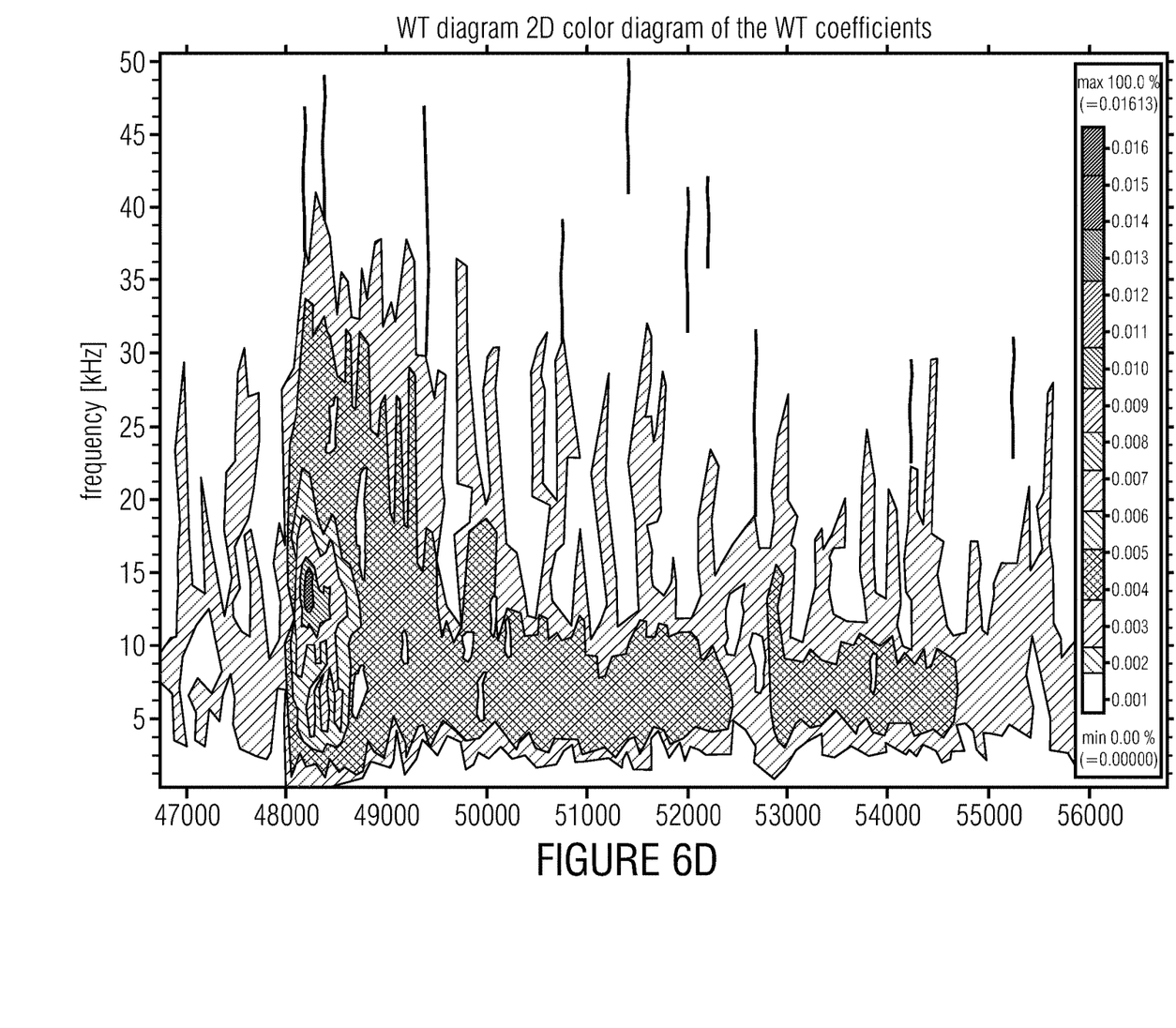
FIG. 6d shows a spectrogram of the detected signal shown in FIG. 6c.

FIG. 6d shows a spectrogram of the detected signal shown in FIG. 6c. In FIG. 6d, the ordinate describes the frequency in kHz, while the abscissa describes time in s, and the color and/or hatching gradient describes the normalized signal amplitude in %.

Further embodiments thus provide a device for detecting pests (e.g., storage pests such as beetles, moths, larvae, for example) in all stages of development in granular bulk material (e.g., grain, corn, leguminous plants, etc.) having diameters between 0.5 mm and 20 mm. The bulk material consists of different grains of the same type and having similar grain sizes.

When sending and receiving sound signals, the natural frequencies of the grains of the bulk material may be exploited for detecting the pest infestation and the grain properties. Grains have characteristic natural frequencies which correspond to their dimensions and their internal structures and also correlate with the moisture of the grains.

Excitation may take place at the characteristic natural frequency of the grains of the bulk material by means of the actuators. The excitation frequency ranges from 1 Hz to 5 MHz, advantageously from 10 kHz to 2 MHz, particularly advantageously from 100 kHz to 1 MHz.

In this context, differences in the natural frequencies between full, non-infested grains and hollow, infested grains can be recognized.

Reception of bulk-material oscillations may take place within the frequency range from 10 Hz to 5 MHz, advantageously 10 kHz to 2 MHz, particularly advantageously 100 kHz to 1 MHz.

Detection of pest infestation may be determined by periodically activating and/or stopping the pest activity by means of the followings steps:

emitting acoustic waves ranging from 1 Hz to 20 kHz, advantageously 10 Hz to 10 kHz, particularly advantageously 10 Hz to 1 kHz;

receiving the sound noises within the bulk material with and without additional noise input within the frequency range from 1 Hz to 20 kHz, advantageously 10 Hz to 20 kHz (FIGS. 6a to 6d);

calculating the difference between both states in order to eliminate the ambient noises;

using up to 10 receivers simultaneously within the area of the bulk material, but at least one transmitter and one receiver.

Pest infestation may be detected by an automatic sampling device or by a hand-held instrument by means of immersion into the bulk material. Said immersion takes place, at different locations, 1 to 100 times, advantageously 3 to 30 times, particularly advantageously 5 to 10 times.

Fixedly installed silo monitoring may detect pest infestation by emitting sound signals within the low-frequency range from 10 Hz to 1 kHz for stopping or activating pest activity, and reception of pest activity may occur within the frequency range from 1 kHz to 20 kHz.

Even though some aspects have been described within the context of a device, it is understood that said aspects also represent a description of the corresponding method, so that a block or a structural component of a device is also to be understood as a corresponding method step or as a feature of a method step. By analogy therewith, aspects that have been described within the context of or as a method step also represent a description of a corresponding block or detail or feature of a corresponding device. Some or all of the method steps may be performed by means of a hardware device (or while using a hardware device), such as a microprocessor, a programmable computer or an electronic circuit. In some embodiments, some or several of the most important method steps may be performed by such a device.

Depending on specific implementation requirements, embodiments of the invention may be implemented in hardware or in software. Implementation may be effected while using a digital storage medium, for example a floppy disc, a DVD, a Blu-ray disc, a CD, a ROM, a PROM, an EPROM, an EEPROM or a FLASH memory, a hard disc or any other magnetic or optical memory which has electronically readable control signals stored thereon which may cooperate, or cooperate, with a programmable computer system such that the respective method is performed. This is why the digital storage medium may be computer-readable.

Some embodiments in accordance with the invention thus comprise a data carrier which comprises electronically readable control signals that are capable of cooperating with a programmable computer system such that any of the methods described herein is performed.

Generally, embodiments of the present invention may be implemented as a computer program product having a program code, the program code being effective to perform any of the methods when the computer program product runs on a computer.

The program code may also be stored on a machine-readable carrier, for example.

Other embodiments include the computer program for performing any of the methods described herein, said computer program being stored on a machine-readable carrier. In other words, an embodiment of the inventive method thus is a computer program which has a program code for performing any of the methods described herein, when the computer program runs on a computer.

A further embodiment of the inventive methods thus is a data carrier (or a digital storage medium or a computer-readable medium) on which the computer program for performing any of the methods described herein is recorded.

A further embodiment of the inventive method thus is a data stream or a sequence of signals representing the computer program for performing any of the methods described herein. The data stream or the sequence of signals may be configured, for example, to be transferred via a data communication link, for example via the internet.

A further embodiment includes a processing means, for example a computer or a programmable logic device, configured or adapted to perform any of the methods described herein.

A further embodiment includes a computer on which the computer program for performing any of the methods described herein is installed.

A further embodiment in accordance with the invention includes a device or a system configured to transmit a computer program for performing at least one of the methods described herein to a receiver. The transmission may be electronic or optical, for example. The receiver may be a computer, a mobile device, a memory device or a similar device, for example. The device or the system may include a file server for transmitting the computer program to the receiver, for example.

In some embodiments, a programmable logic device (for example a field-programmable gate array, an FPGA) may be used for performing some or all of the functionalities of the methods described herein. In some embodiments, a field-programmable gate array may cooperate with a microprocessor to perform any of the methods described herein. Generally, the methods are performed, in some embodiments, by any hardware device. Said hardware device may be any universally applicable hardware such as a computer processor (CPU), or may be a hardware specific to the method, such as an ASIC.

While this invention has been described in terms of several embodiments, there are alterations, permutations, and equivalents which fall within the scope of this invention. It should also be noted that there are many alternative ways of implementing the methods and compositions of the present invention. It is therefore intended that the following appended claims be interpreted as including all such alterations, permutations and equivalents as fall within the true spirit and scope of the present invention.

The invention claimed is:

1. A device for acquiring information about a pest or several pests within a bulk material, comprising:
    an actuator for outputting an excitation signal not exceeding 500 kHz that is suitable to excite the pest or the pests;
    a sensor for detecting a signal generated in response to the excitation, so as to acquire a detected signal; and
    an evaluator for evaluating the detected signal so as to acquire the information about the pest(s) within the bulk material;
    wherein at least one out of the actuator and the sensor is implemented by means of an electronic device,
    wherein the evaluator is implemented by means of a processor or electronic device
    wherein the actuator is configured to tune a frequency of the excitation signal to a resonant frequency of the bulk material.

2. The device as claimed in claim 1, wherein the generated signal is generated by the pest(s) in reaction to the excitation signal.

3. The device as claimed in claim 2, wherein the generated signal is dependent on a resonant frequency of the bulk material, the resonant frequency of the bulk material being dependent on an infestation of the bulk material with the pest(s).

4. The device as claimed in claim 1, wherein the actuator is configured to output the excitation signal at a frequency ranging from 1 Hz to 5 MHz.

5. The device as claimed in claim 1, wherein the sensor is configured to detect the generated signal at a frequency ranging from 10 Hz to 5 MHz.

6. The device as claimed in claim 1, wherein the sensor is further configured to detect a reference signal that is independent of the excitation, so as to acquire a detected reference signal;
    wherein the evaluator is further configured to evaluate the detected reference signal so as to acquire the information about the pest(s) within the bulk material.

7. A system, comprising:
    a device as claimed in claim 1; and
    an accommodator for accommodating a commodity, the device being arranged at or within the accommodator such that a commodity accommodated by the accommodator can be monitored by means of the device; or
    an accommodator for accommodating one or more living beings, the device being arranged at or within the accommodator such that one or more living beings can be monitored by means of the device.

8. A method of acquiring information about a pest or several pests within a bulk material, the method comprising:
    outputting an excitation signal not exceeding 500 kHz suitable to excite the pest(s);
    detecting a signal generated in response to the excitation, so as to acquire a detected signal; and
    evaluating the detected signal so as to acquire the information about the pest(s) within the bulk material;
    wherein at least one out of the outputting the excitation signal and the detecting the signal generated in response to the excitation is implemented by means of an electronic device, and
    wherein the evaluating the detected signal is implemented by means of a processor or electronic device
    wherein a frequency of the excitation signal is tuned to a resonant frequency of the bulk material.

9. A non-transitory digital storage medium having a computer program stored thereon to perform the method according to claim 8 when said computer program is run by a computer.

* * * * *